United States Patent [19]

Tanabe et al.

[11] Patent Number: 5,443,454
[45] Date of Patent: Aug. 22, 1995

[54] CATHETER FOR EMBOLECTOMY

[75] Inventors: Susumu Tanabe; Fumihisa Hirose, both of Nakai, Japan

[73] Assignee: Terumo Kabushiki Kaisha, Tokyo, Japan

[21] Appl. No.: 164,218

[22] Filed: Dec. 9, 1993

[30] Foreign Application Priority Data

Dec. 9, 1992 [JP] Japan ................................. 4-329722

[51] Int. Cl.⁶ ........................ A61M 5/00; A61M 25/00
[52] U.S. Cl. .................................... 604/264; 604/52; 604/82; 660/106
[58] Field of Search ................. 606/106; 604/21, 264, 604/266, 280, 282, 52, 82, 83, 85

[56] References Cited

U.S. PATENT DOCUMENTS

| | | | |
|---|---|---|---|
| 4,551,132 | 11/1985 | Pasztor et al. | 604/52 |
| 4,840,622 | 6/1989 | Hardy | 604/264 |
| 4,932,942 | 6/1990 | Maslanka | 604/83 |
| 4,994,069 | 2/1991 | Ritchert et al. | 606/200 |
| 5,211,627 | 5/1993 | William | 604/82 |
| 5,308,342 | 5/1994 | Sepetka | 604/264 |
| 5,318,524 | 6/1994 | Morse et al. | 604/82 |
| 5,322,510 | 6/1994 | Lindrer | 604/82 |

FOREIGN PATENT DOCUMENTS

| | | |
|---|---|---|
| 61-161220 | 7/1986 | Japan . |
| 4-20348 | 1/1992 | Japan . |
| 4-197359 | 7/1992 | Japan . |

OTHER PUBLICATIONS

Igaku No Ayumi, [SIC.]vol. 153, No. 11, p. 635, Jun. 1990 Ishiyaku Publishers, Inc., "Embolization Technique of Cerebral Arterial Aneurysm Advantages and Disadvantages of Embolization Technique and Surgical Operation".

Igaku No Ayumi, [SIC.] vol. 154, No. 7, p. 432, Aug. 1990 Ishiyaku Publishers, Inc., "Situation of New Subspeciality of Neurosurgery".

Neurosurgeons 9, 229–239, Sep. 1990, K. Goto, "Recent Advances and Future Problems of Interventional Neuroradiology".

Medical Tribune, pp. 46≧47, Oct. 1989, K. Taki, "Possibility and Limit of Intravascular Surgery", Nippon Accel Shubringer Shuppan, K.K.

Neuroradiology, (1991) 33 [Suppl]: 193–194, Springer-Verlag Oct. 1991 "A New Technique for Embolization of Cerebal Arteriovenous Malformations and Dural Arteriovenous Fistulae", K. Goto et al.

Journal of Biomedical Materials Research, vol. 17, 167–177 (1983) John Wiley & Sons, Inc., "Isobutyl 2-Cyanoacrylate as an Osseous Adhesive in the Repair of Osteochondral Fractures", Marion C. Harper.

J. Neurosurg, vol. 41, Aug. 1974, 125–145, F. A. Serbinenko, M. D. American Associate of Neurological Surgeons Dartmouth Medical School, "Balloon Catheterization and Occlusion of Major Cerebral Vessels".

"The Eleventh General Meeting of Japan Biomaterial Society Collecton of Spripts for Presentation", Taki et al., Oct. 1989, At Kyoto University, Chief of the 11th Meeting: Takao Yamamuro.

Primary Examiner—C. Fred Rosenbaum
Assistant Examiner—Chalin Smith
Attorney, Agent, or Firm—Frishauf, Holtz, Goodman, Langer & Chick

[57] ABSTRACT

An embolectomy catheter containing a lumen for the introduction of a liquid substance and provided in the distal end thereof with spinning means for extruding said liquid substance in the form of a filamentous embolic material.

22 Claims, 6 Drawing Sheets

CATHETER FOR EMBOLECTOMY

BACKGROUND OF THE INVENTION

1. Field of the Invention

This invention relates to a catheter for use in vascular embolectomy.

2. Description of the Prior Art

As a common therapy for cerebral aneurysm, a method which comprises craniotomy and clipping the neck of aneurysm has existed to date. Since this method is highly susceptible of surgical invasion, the possibility of this method entailing a complication is undeniable. For the purpose of improving the results of therapy for morbidities in the cerebral blood vessels such as large aneurysms which render surgical operations impossible or difficult and alleviating the physical, spiritual, and economic burdens on the part of patients, the intravascular surgical therapy which uses a vascular catheter without inducing a surgical invasion has been gaining in impetus (Katsuya Goto, "Neurosurgeons," 9, 229–239, 1990).

The intravascular surgical therapy effects the cure of a morbidity in the cerebral blood vessel, for example, by inserting a miniature catheter extremely selectively into the affected part of the cerebral artery and occluding a cerebral aneurysm with an embolic material which is introduced by the catheter.

The cerebral blood vessel lacks the external elastic membrane and possesses only a thin vascular wall as compared with other parts of the brain and, therefore, offers weak resistance to the lateral pressure of bloodstream. Inside the cranium, the blood vessels run intricately. Particularly in a patient of hypertension, the ramified parts of such blood vessels are liable to sustain an injury from the pressure exerted thereon. The statistics on anatomical examinations indicate that the cerebral aneurysms are aneurysms occurring in the artery system in one out of 100 adults and have a wide shape distribution approximately ranging from 1 mm to more than 20 mm in diameter and that the cites of genesis are widely varied over cerebral arteries with the Willis ring as the center. When the cerebral aneurysms are fractured, they cause such serious cerebrovascular injuries as subarachnoid hemorrhage and intracerebral hemorrhage. When they grow gigantically in size, they induce the compression symptom of the cerebral nerves. Arteriovenous malformations abound most in all the malformations of the cerebral blood vessels and are widely known. They are an aggregate of zigzagging and dilated influent and effluent blood vessels and arteriovenously inosculated blood vessels intervening therebetween. Clinically, they form an important cause for intracerebral hemorrhage, epilepsy, and progressive nervous breakdown which reach crisis in relatively young patients.

The embolectomy cures such a morbid alteration in the cerebral artery as mentioned above by occluding the affected part with an occluding substance thereby blocking the bloodstream in the affected part and solidifying the site of disease. The solidified site of disease, when necessary, is excised.

The cure of cerebral arteriovenous deformations has now reached the point where the embolectomy plays the main role in therapy (Goto K. et al., Neuro radiology, 33, [Suppl] 193–194, 1991). This situation is expected to prevail in the cure of cerebral aneurysms in the near future (Katsuya Goto, "Walks of Medicine," 153; 635, 1990). The trend has encouraged scientists to search various substances for embolic materials.

Heretofore, cyano-acrylate type materials have been in popular use as liquids for occluding sites of morbid alteration in the blood vessels (J. Biomed. Mater. Res., 17, 167–177 (1983)M. C. Harpers et al.).

Recently, it has been proposed to adopt the dimethyl sulfoxide (DMSO) solution of an ethylene-vinyl alcohol copolymer (a commercial product marketed under trademark designation of "Eval") as an embolic material and allow the DMSO to be diffused in the blood and the Eval to precipitate and occlude the blood vessel (Medical Tribune, Oct. 26, 1989, pp. 46 and 47).

Meanwhile, the method which comprises inserting a catheter accompanied by a separable balloon into an aneurysm, inflating the balloon thereat and occluding the aneurysm, and allowing the inflated balloon to indwell inside the aneurysm has found popular acceptance (Journal of Neurosurgery, 41, 125–145 (1974), F. A. Serbinenko).

Other means heretofore adopted for the therapy in question include metallic coils (minicoils), polyvinyl alcohol (PVA) sponges, alcohols, and sutures which have been selectively used to suit particular objects of therapy.

The conventional cyano-acrylate type embolic material is injected into the site of aneurysm with difficulty because it quickly undergoes curing polymerization in the blood vessel. For the purpose of preventing the catheter from being stuck to the interior of the cerebral blood vessel with this material which is capable of manifesting a powerful adhesive action, the catheter inserted into the blood vessel must be extracted at a stroke as soon as the injection of the material into the site of disease is completed. Thus, the material allows no easy handling. The injection cannot be repeated even when the occlusion obtained at all turns out to be imperfect. This embolic material is further at a disadvantage in inflicting a grave stimulus to the wall of the blood vessel and inducing a strong inflammatory reaction.

In the system using Eval dissolved in the DMSO solvent, part of the solvent remains persistently in the central part of the mass of Eval which has been precipitated on contact with the bloodstream. When this system is used in the treatment of the aneurysm by the embolectomy, the disadvantage arises that the part of the material which has leaked into the blood vessel from the exit side of the aneurysm adheres to the branched part of the blood vessel along the path of the bloodstream.

No safety has been established yet for the DMSO as the solvent [Hiroo Iwata et al., Collection of Scripts for Presentation at the 11th General Meeting of Japan Biomaterial Society (1989), 68, II-22]. Further, the solvent exerts an injury to utensils made of resinous materials. When the system is used in the manner of directly injecting the solution into the site of aneurysm through the medium of a catheter as described above, it is not perfectly safe to regard the solvent optimum.

More often than not, the separable balloon is adopted in the treatment of the aneurysm by the embolectomy. When the balloon is used at all, since the reaction between the balloon and the inner wall of the aneurysm is weak, the possibility that the inflated balloon will not thoroughly fill out the empty cavity inside the aneurysm and the disease will recur if even a small portion of the empty cavity remains unfilled is high. An attempt to fill up amply the inner cavity of the aneurysm by inflating the balloon to the largest possible volume results in increasing the inner pressure of the balloon possibly to the extent of altering the shape of the aneurysm and rupturing the aneurysm. The separation of the inflated balloon from the catheter requires application of tractive force to the catheter and exalts the possibility of fracturing the aneurysm.

At the present time, perfect isolation of the site of aneurysm is difficult to achieve by the method which resorts to the use of the separable balloon or a minicoil. Thus, the method of proximal occlusion which comprises partially occluding the parental artery is adopted more often than not [Akira Takahashi, "Walks of Medicine," 154, (7), 432, (1990)]. This method, however, exposes the brain to the possibility of hindering the bloodstream because it requires to sacrifice the parental artery. The method which resorts to simultaneous use of a separable balloon and minicoils has been proposed for the treatment of a gigantic aneurysm by the embolectomy (Katsuya Goto, Collection of Excerpts for Presentation at the Study Meeting of Japan Angiography IVR, 1991). This method requires to use many expensive minicoils, consumes much time, and lacks in the effect of reducing pressure. In other words, it is at a disadvantage in offering low packing density and encountering difficulty in decreasing the inner pressure of the aneurysm immediately after the balloon has been indwelt.

Besides, such materials as PVA granules, alcohols, and sutures entail many therapeutic problems such as difficult handling and insufficient effect of treatment.

It is, therefore, a primary object of this invention to provide for an embolectomy catheter which permits the embolectomy to be performed safely and infallibly on an aneurysm.

A further object of this invention is to provide an embolectomy catheter which allows formation of an embolic material capable of restraining diffusion of minute fragments thereof within the blood vessel.

Another object of this invention is to provide an embolectomy grade catheter which permits formation of a filamentous embolic material.

Still another object of this invention is to provide an embolectomy catheter which permits formation of an embolic material aimed at a morbid alteration of the blood vessel and adapted to restrain a secondary reaction, if any, of a solvent used in the material to the fullest possible extent.

Yet another object of this invention is to provide an embolectomy catheter which offers a high filling density and permits a reduction in the inner blood pressure of aneurysm immediately after the embolic material has been introduced.

Throughout this specification, the term "spinning means" or the like is used generally to define any type of device for producing a filamentous material, such as an extruder, a nozzle, a device to impart shear stress to the extruded material to "spin" the material, etc.

SUMMARY OF THE INVENTION

These objects are fulfilled by the embolectomy catheter of this invention. Specifically, these objects are accomplished by an embolectomy catheter which is possessed of a lumen for introducing a liquid substance and is provided at the distal end thereof with a filament forming device (i.e., a spinning means) for shaping the liquid substance in the form of a filamentous embolic material. The lumen for the introduction of the liquid substance is desired to be provided with openings one each at the distal end and the basal end part of the catheter body.

The embolectomy catheter of this invention is desired to be provided further with at least one lumen to be disposed separately of the aforementioned lumen for the introduction of the liquid substance. The spinning means or filament forming device is provided with discharge means. The liquid substance comprises a reactive liquid substance and other liquid substance capable of reactively hardening the reactive liquid substance just mentioned. These component liquid substances are separately introduced to the distal end of the catheter via respective independent lumens. Preferably, the aforementioned spinning means or filament forming device effects the formation of the filamentous embolic material by mixing the reactive liquid substance with the other liquid substance capable of reactively hardening the reactive liquid substance.

For the embolectomy catheter of this invention, it is preferable that the liquid substance is a photoreaction type liquid substance which is hardened by exposure to light and the spinning means is provided with light exposure means which is capable of reactively hardening the photoreaction type liquid substance. The liquid substance forms the filamentous embolic material by virtue of shearing stress and the spinning means, therefore, is desired to be provided with a shearing stress-imparting means which is capable of imposing shearing stress on the liquid substance. The filaments to be produced by the spinning are desired to have a thickness in the range of 1 to 100 deniers.

The embolectomy catheter of this invention comprises a reservoir part disposed in the catheter body, pressure exerting means for exerting pressure on the reservoir part, a lumen for intercommunication between the exterior of the catheter body and the reservoir part, and means for conversion of the mobile liquid substance stored in the reservoir part into a continuous filament. Further, the embolectomy catheter of this invention is such that the main body thereof is relatively hard and the distal end thereof is relatively soft and is adapted to form and emit a filamentous embolic material.

Since this invention provides the embolectomy catheter at the distal end thereof with spinning means for manufacturing a spinning liquid substance into a filamentous embolic material, it permits use of this filamentous embolic material for the cure of an aneurysm by embolectomy and brings about an effect of eliminating such heretofore prevalent drawbacks as leakage of an embolic material out of the site of aneurysm and infliction of injury on the feeble wall of the aneurysm by the embolic material and allowing the treatment by embolectomy to be performed safely and infallibly.

Since the filamentous embolic material which is extrusion molded by the catheter possesses continuity, it has no possibility of finely dispersing and leaking out of the aneurysm.

Further, since the filamentous embolic material gathers into a round mass, it is free from such a possibility of powerfully pressing the wall of the aneurysm subsequently to the introducing of the embolic material in the aneurysm and consequently fracturing the aneurysm as is attendant on the conventional embolizing means like balloons, metallic coils, and polymers of EVA. Further, since the round mass has high filling density, it allows the inner pressure of the aneurysm to be decreased immediately after the embolic material has been introduced in the aneurysm.

When the filamentous embolic material is made of a substance abounding in affinity for or reactivity with the inner wall of the aneurysm, this material can adhere fast to the wall of the aneurysm and, at the same time, the round mass can react with the blood and form a coagulated mass and effect perfect occlusion of the aneurysm.

The embolectomy catheter is possessed of at least one lumen separately of the lumen for the introduction of the liquid substance. This additional lumen can serve as a passageway for a guide wire or an endoscope and consequently facilitate the introduction of the catheter into the site of therapy. The endoscope permits ready inspection of the embolic material in process of manufacture by extrusion molding.

The discharge means provided in the spinning means fixes the direction in which the extruded filament is spouted out and serves to adjust this direction in conformity to the direction of the distal end of the catheter and, therefore, enables the filament to be discharged at a various position inside the cerebral aneurysm and gathered into a uniformly rounded mass.

Further, the liquid substance is composed of a reactive liquid substance and other liquid substance capable of reactively hardening the reactive liquid substance and these component liquid substances are separately introduced to the distal end of the catheter via their respective lumens. The spinning means forms the filamentous embolic material by mixing the reactive liquid substance with the other liquid substance capable of reactively harding the reactive liquid substance and, as a result, facilitates the introduction of the liquid substances to the distal end of the catheter and ensures easy handling of the liquid substances.

Since the reactive liquid substance is a photoreaction type liquid substance which hardens on exposure to light and the spinning means is provided with the light exposure means which is capable of reactively hardening the photoreaction type substance, the reactive liquid substance can retain the liquid state intact until immediately before the spinning and the spinning of the liquid substances can be easily terminated by simply blocking the incident light.

Further, since the liquid substances form the filamentous embolic material by virtue of shearing stress and the spinning means is provided with shearing stress-imparting means adapted to exert shearing stress on the liquid substances, the liquid substances can retain the liquid state intact until immediately before the spinning and the spinning can be easily terminated by simply ceasing the exertion of the shearing stress.

Since the thickness of the extruded filament is fixed in the range of 1 to 100 denlets, the filament easily gathers into the round mass which is soft and liable to form a coagulated mass. Thus, the cerebral aneurysm is occluded infallibly.

The catheter for embolectomy in accordance with the present invention can also be used for treating, for example, other blood vessel such as esophageal varices, other aneurysms excluding cerebrovascle, e.g., aortic aneurysm. It can be also be used for treating disease, for example, and prosthesis method in lumen and ventor such as for prosthese of a removed portion after cutting a tissue such as cancer and tumor by surgical operation using in endoscope.

EXPLANATION OF THE PREFERRED EMBODIMENT

An embolectomy catheter of this invention will be described below specifically with reference to preferred embodiments.

Figure 1A:
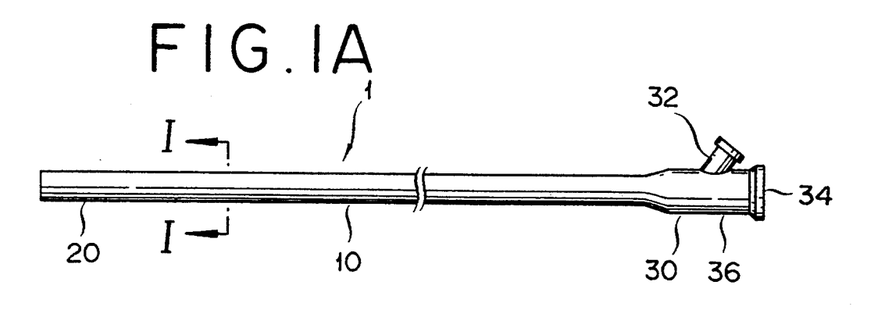
FIG. 1A is an overall diagram of an embolectomy grade catheter according with this invention.

An embolectomy grade catheter 1 of this invention illustrated in FIG. 1A comprises a main body part 10 of catheter, a distal end 20 of catheter, and a proximal end (operating part) 30 of catheter. The proximal end 30 comprises a hub 36 which a liquid substance introducing port 32 and a guide wire port 34. Preparatory to use, the liquid substance introducing port 32 as a basal end part opening is connected to a container keeping a liquid substance in store and pressure-exerting means is operated to exert pressure on the liquid substance and induce emission of a thin continuous material through the distal end 20 as described specifically hereinbelow.

Figure 1B:
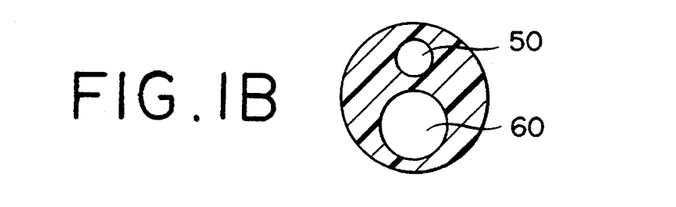
FIG. 1B is a magnified cross section taken through FIG. 1A along the line I—I.

FIG. 1B is a cross section of the main body part 10 of catheter. As illustrated in the diagram, the main body 10 of catheter is provided with a lumen 50 for introducing the liquid substance, namely the lumen 50 for introducing the liquid substance through the introducing port 32 of the proximal end 30 of catheter and supplying it to the exterior of the catheter 1 through the distal end thereof and a lumen 60 to be used for insertion therein of a guide wire or an endoscope. The catheter 1 is provided on the surface thereof with a coating layer (not shown) endowed with biocompatibility and lubricity. The bioadaptable and lubricious coating layer precludes the formation of thrombus on the catheter surface, prevents the inner membrane of blood vessel from sustaining injury possibly inflicted by the catheter, and degrades the friction of the catheter with the inner wall of blood vessel to the extent of allowing the catheter to advance smoothly inside the blood vessel.

Figure 2A:
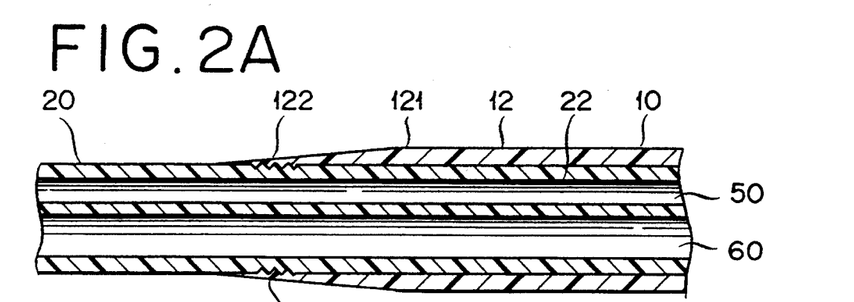
FIG. 2A is a cross section of the embolectomy grade catheter of this invention.
Figure 2B:
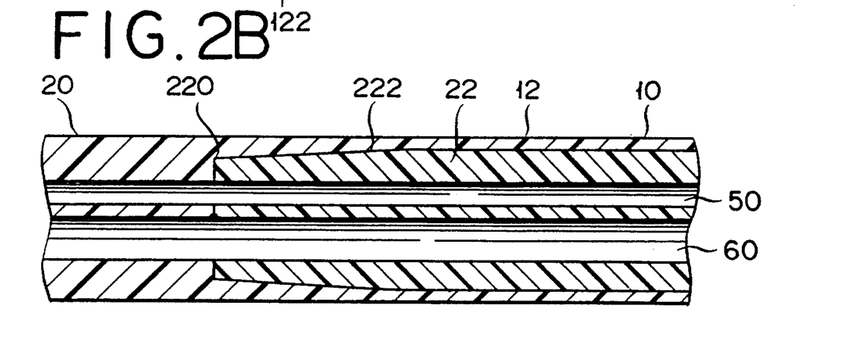
FIG. 2B is a cross section of an embolectomy catheter as another embodiment of this invention.

FIGS. 2A and 2B are a cross section illustrating the boundary part between the main body 10 and the distal end 20 of the embolectomy grade catheter of this invention. In FIG. 2A, the left side on the plane of paper constitutes the distal end 20 of the catheter 1 and the right side the main body part 10. The main body 10 is provided internally with an inner layer part 22 and externally with an outer layer part 12 both relative to the direction of diameter of the cross section thereof. In the main body 10, the outside diameter and thickness of the outer layer part 12 are substantially identical throughout the axial direction. The outside diameter of the inner layer part 22 is substantially identical in the axial direction. The distal end 20 has the outer surface thereof formed of an extension of the inner layer part 22 of the main body part 10. The outer layer part 12 has the distal end thereof positioned at the basal end of the distal end 20 and does not cover the distal end 20. The outer layer part 12 is formed of a hard material having relatively high rigidity and the inner layer part 22 is formed of a relatively soft material. In the inner layer part 22, the lumen 50 for introducing the liquid substance is formed. Further in the inner layer part 22, the lumen 60 intended for insertion therein of a guide wire or an endoscope is formed as other passageway separated from the lumen 50 for the introduction of the liquid substance.

The outer layer part 12 has a substantially uniform thickness as far as a proximity 121 of the distal end thereof. The outside diameter of the outer layer part 12 is decreased from this proximity 121 toward the distal end so as to buffer a sudden change of the physical property (rigidity) between the main body 20 including the outer layer part 12 of relatively high rigidity and the distal end 10 formed exclusively of the relatively soft inner layer part 22. The distal end 10 is soft and the main body 10 is highly rigid and they share the boundary part whose softness increases toward the distal end. This elaborate distribution of softness prevents the boundary part from being kinked. Further, the outer layer part 12 is prevented from forming a kink therein by giving to the inner surface of the proximity 121 of the distal end a spiral or annular incision not so deep as to reach the outer surface of the outer layer part 12. By giving the spiral or annular incision to the inner surface as described above or by roughing the inner surface, the fusion between the outer surface of the inner layer part 22 and the inner surface of the proximity 121 of the distal end is prevented from being broken. The inner layer part 22 of the distal end 20 is so constructed that the outside diameter thereof is substantially uniform or is decreased toward the distal end.

In FIG. 2B as in FIG. 2A, the left side on the plane of paper constitutes the distal end 20 of the catheter 1 and the right side the main body part 10. In FIG. 2B and FIG. 2A, like parts are denoted by like reference numerals. The main body part 10 is provided internally with the inner layer part 22 and externally with the outer layer part 12, both relative to the direction of diameter of the cross section. In the main body part 10, the outside diameter and the thickness of the outer layer part 12 are substantially uniform in the axial direction. The outside diameter of the inner layer part 22 is also substantially uniform in the axial direction. In the distal end 20, the main body part 10 has the outer layer part 12 thereof formed of an extension on the distal end side of the inner layer part 22. The inner layer part 22 has a distal end 220 thereof as its terminal. The outer layer part 12 is formed of a relatively soft material and the inner layer part 22 is formed of a material of relatively high rigidity. In the outer layer part 12 of the distal end 20 of the inner layer part 22 of the main body part 10, the lumen 50 for introducing the liquid substance and the lumen 60 for allowing insertion therein a guide wire or an endoscope are formed continuously in the axial direction.

A proximity 222 of the distal end of the inner layer part in the main body part has the outside diameter decreased toward the distal end thereof so as to buffer a sudden change in the physical property (rigidity) between the main body part 20 including the inner layer part 22 of relatively high rigidity and the distal end 10 formed exclusively of the relatively soft outer layer part 12 and preclude formation of a kink. By giving to the outer surface of the proximity 222 of the distal end of the inner layer part 22 a spiral or annular incision not so deep as to reach the lumens 50 and 60, the softness can be increased in the direction of the distal end and the formation of a kink can be precluded. By giving the spiral or annular incision as described above or by roughing the inner surface, the fusion between the inner surface of the outer layer part 12 and the outer surface of the proximity 222 of the distal end is rendered less susceptible to breakage. The inner layer part 22 of the distal end 20 is so constructed that the outside diameter thereof is substantially uniform or is decreased toward the distal end.

Figure 3:
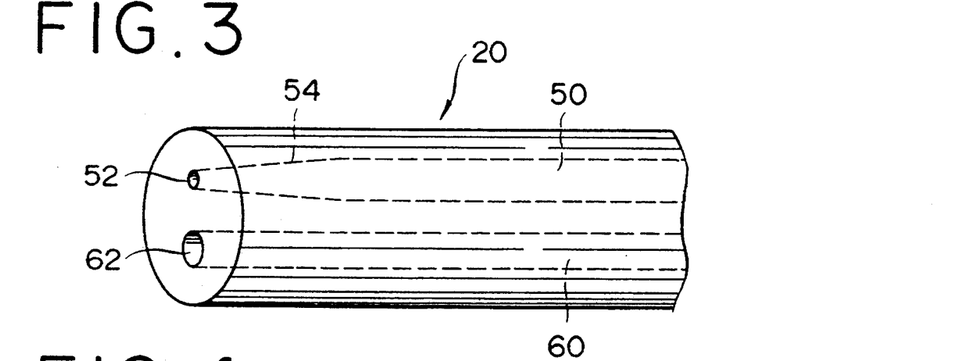
FIG. 3 is a perspective view of the distal end of the embolectomy grade catheter of this invention.

FIG. 3 illustrates the distal end 20 of the embolectomy catheter of this invention. In the distal end 20 of the catheter, a discharge nozzle 54 continuing from the lumen 50 for introducing the liquid substance and, to serve as spinning means, provided with a discharge orifice 52 adapted to effect extrusion molding of the introduced liquid substance and an opening 62 of the lumen 60 for allowing insertion therein of a guide wire or an endoscope are formed. The distal end 20 of the catheter is given an outside diameter of about 1 mm.

The discharge nozzle 54 is so constructed that the inside diameter of the lumen 50 for introducing the liquid substance decreases to the inside diameter of the discharge orifice 52. This decrease of the inside diameter is intended to give a desired outside diameter to the filamentous embolic material being manufactured by extrusion molding and to increase the speed at which the introduced liquid substance is emitted through the discharge orifice 52 by application of pressure. The provision of the discharge nozzle 54 as the spinning means permits formation of a continuous solid material of a minute diameter. So long as the discharge nozzle is given a substantially smaller opening than the inside diameter of the lumen 50, it does not need to be tapered off to effect the formation of the filamentous embolic material.

Figure 4:
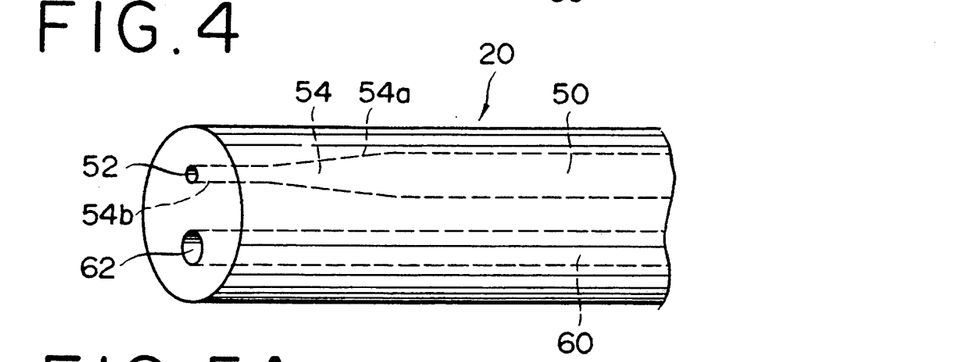
FIG. 4 is a perspective view of the distal end of the embolectomy grade catheter of this invention.

FIG. 4 depicts a first modification of the distal end 10 of the catheter of this invention illustrated in FIG. 3. In the distal end 20, the lumen 60 for allowing insertion therein of a guide wire or an endoscope and the opening 62 thereof are identical with those of the embodiment of FIG. 3 and the discharge nozzle 54 is different from that of the embodiment just mentioned. Specifically, the discharge nozzle 54 of FIG. 4 comprises a part 54a having an inside diameter gradually decreased toward the distal end from the inside diameter of the lumen 50 for introducing the liquid substance, a discharge lumen 54b preceding the part 54a and having an inside diameter substantially uniform and smaller than that of the lumen 50, and the discharge orifice 52 preceding the discharge lumen 54b and forms spinning means. The discharge lumen 52 formed in the length described above functions to impart a substantially fixed outside diameter to the fine embolic material discharged in the form of a filament through the discharge orifice 52.

Figure 5A:
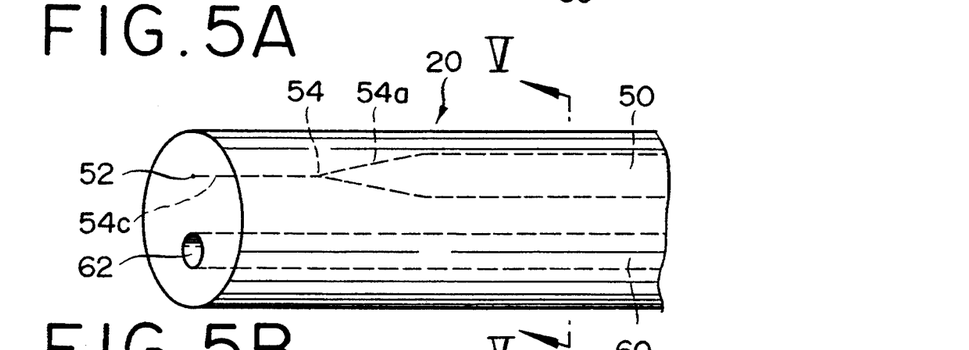
FIG. 5A is a perspective view of the distal end of the embolectomy grade catheter of this invention.
Figure 5B:
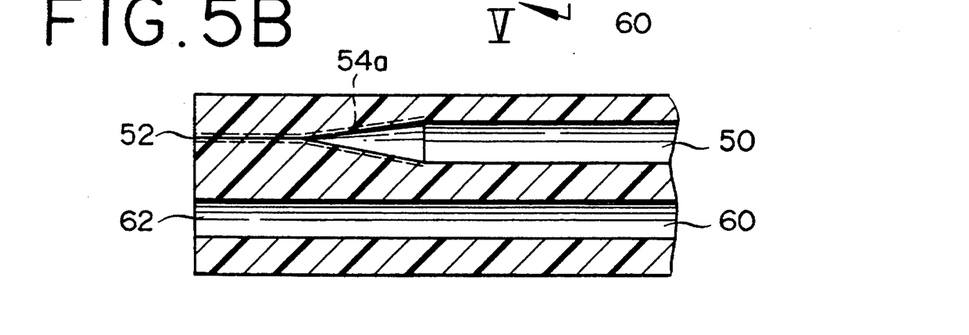
FIG. 5B is a cross section taken through FIG. 5A along the line V—V.

FIGS. 5A and 5B depict a second modification of the distal end 20 of the catheter 1 of this invention. The discharge nozzle 54 of FIG. 5A intended as spinning means comprises the part 54a having an inside diameter gradually decreased toward the distal end from the inside diameter of the lumen 50 for introducing the liquid substance and an occluded lumen 54c adapted to open itself and give rise to a passageway and permit emission of the filamentous embolic material through the discharge orifice 52 by virtue of the elasticity of the material forming the distal end 20 of catheter when the pressure exerted on the occluded lumen 54c from the lumen 50 side is increased.

FIG. 5B is a cross section of the distal end 20 of FIG. 5A. The discharge orifice 52 and the occluded lumen 54c normally remain in a closed state. When the lumen 50 is filled with the liquid substance as the raw material for the embolic material and the inner pressure thereof is increased as a result, the increasing inner pressure is imposed on the inner wall of the part 54c having the diameter thereof gradually decreased toward the distal end thereof and the occluded lumen 54c is made to open a passageway as indicated by a broken line in the diagram. The occluded discharge orifice 52 similarly expands radially and consequently allows the liquid substance to advance through the passageway to be formed by the occluded lumen 54c and undergo extrusion molding due to the passage through the discharge orifice 52 and form a solid filament. When the liquid substance happens to be such that it assumes the filamentous form on contact with blood, this liquid substance is desired to be kept from contact with blood until it is extruded through the discharge orifice. Particularly when the liquid substance is a solution having a solute dissolved in a solvent, the contact of this liquid substance with blood entails dispersion of the solvent because the embolic material is produced owing to the dispersion of the solvent and the attendant deposition of the solute. When the solute happens to be insoluble in blood, it separates from the solution and assumes a given shape. Thus, the blood-insoluble elute is desired not to contact blood before the extrusion molding is started. Since the occluded lumen 54c is closed by lowering the inner pressure thereof, the operation of embolectomy can be resumed at any time after an interruption.

Figure 6:
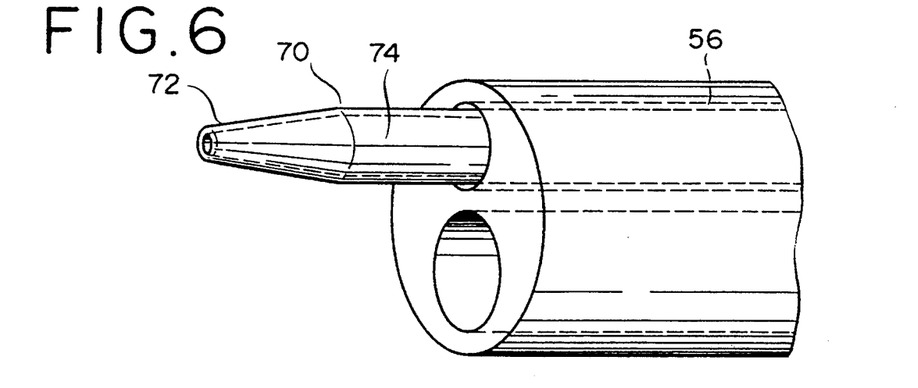
FIG. 6 is a perspective view of the distal end of the embolectomy grade catheter of this invention.

FIG. 6 is a perspective view of the distal end of an embolectomy catheter 1 as another embodiment of this invention. The basic components of this embodiment, namely the main body of catheter, the distal end of catheter, and the proximal end of catheter, are identical with those of the catheter of FIG. 1A. The boundary part between the distal end and the main body may be in either of the constructions illustrated in FIG. 2. A catheter 70 intended to give birth to a filamentous embolic material is inserted first through the lumen 60 adapted to permit insertion therein of a guide wire or an endoscope and then through a lumen 56 which extends from the proximal end through the distal end to the distal end severally of the catheter. The catheter 70 to be used for the formation of the filamentous embolic material is capable of drawing a distal end 72 thereof into the lumen 56 and protruding it to a desired length from the lumen 56. The distal end 72 has a tapered shape. The catheter 70 is provided with a lumen 74 which extends in the axial direction of the catheter 70 from the basal end part (not shown) through the distal end 72. The lumen 74 is a passageway for introducing the liquid substance and allowing the distal end 72 to emit the filamentous embolic material. The lumen 74 has an inner diameter gradually decreased toward the distal end and is consequently enabled to fulfill the function of a nozzle which, as spinning means, imparts a prescribed shape to the extruded filamentous embolic material. The distal end 72 is opened and the opening consequently formed is used to effect continuous discharge of the liquid substance under the pressure exalted inside the lumen 74.

The distal end 72 is desired to be provided with an X-ray contrast medium of gold or platinum to facilitate the detection of the position of the distal end 72 in the blood vessel. When the catheter 70 for the formation of the filamentous embolic material is so disposed as to slide freely with the catheter 1, the position of the distal end 72 of the catheter 70 can be changed even inside the aneurysm in which the catheter 1 has been already indwelt. The round mass of the filamentous embolic material, therefore, can be closely tilled sequentially from the recess to the opening of the aneurysm. The contrast medium disposed in the distal end 72 facilitates the detection of the position of the distal end 72 inside the aneurysm.

Figure 7A:
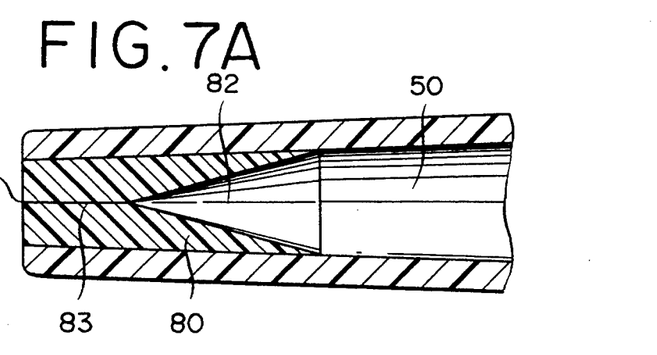
FIG. 7A is a cross section of the distal end of the embolectomy grade catheter of this invention.
Figure 7B:
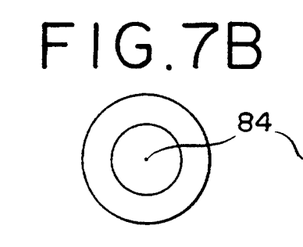
FIG. 7B is a front view of the distal end of the catheter shown in FIG. 7A.

FIGS. 7A and 7B depict the distal end of the embolectomy catheter 1 of this invention as another embodiment of this invention. FIG. 7A is a cross section of the distal end and FIG. 7B a front view of the distal end. In the present embodiment, the basic components, i.e. the main body of catheter, the distal end of catheter, and the proximal end of catheter, are identical with those of the catheter of FIG. 1A and the lumen 50 for the introduction of the liquid substance is occluded on the distal end side thereof with an elastic member 80. In the basal end part of the elastic member 80, a conical empty space radially tapered toward the distal end side thereof is formed concentrically with the elastic member 80. The apical point of the conical empty space 82 constitutes an occluded lumen, which is caused to form a minute passageway when the pressure exerted from the conical empty space 82 side is increased. Owing to this minute passageway, the liquid substance in the lumen 50 is discharged in a filamentous form through a discharge orifice 84. This discharge orifice 84 can be led by this catheter and the guide wire by the lumen 50 respectively into the aneurysm. The elastic member 80 is endowed with elasticity enough to permit insertion and extraction of the guide wire. The present embodiment differs from that of FIGS. 5A and 5B in having the occluding member provided as an independent member. The independence of this occluding member permits the elastic force of the elastic member to be selected irrespectively of the kind of material for the catheter.

Similarly to the embodiment of FIGS. 5A and 5B, the extrusion of the liquid substance proceeds smoothly because the contact of the liquid substance with blood is obstructed by the elastic member 80 before the extrusion. The elastic member 80 remains in a closed state when the inner pressure of the lumen 50 is below a prescribed level. When the catheter is provided at the distal end thereof with an X-ray contrast medium of gold or platinum, the embolectomy can be performed at the site of aneurysm under X-ray observation and, at the same time, the detection of the position of the distal end of the catheter can be facilitated.

The liquid substance to be used in the present embodiment is what is obtained by dissolving a resinous solute insoluble in water (blood) with an organic solvent. This liquid substance, when placed in blood, entails dispersion of the solvent and consequent precipitation of the solute. The solute/solvent combinations which can be effectively used herein include ethylene-vinyl alcohol copolymer/dimethyl sulfoxide, cellulose acetate resin (CAP)/ethanol, and ethylene-vinyl alcohol copolymer/50% normal propane, for example. The concentration of the resinous solute in the solution is in the range of 0.2 to 20%, preferably 1 to 10%. If this concentration is less than 0.2%, the possibility arises that the dispersion of the solvent in the discharged solution does not proceed well and, as a result, the solution does not assume the filamentous form as expected. Conversely, if the concentration exceeds 20%, the possibility ensues that the solution acquires unduly high viscosity and defies extrusion through the discharge orifice.

When the liquid substance which is destined to entail the dispersion of the solvent and the attendant separation of the solute on contact with blood is advanced at an increased speed and allowed to form a filament of relatively small thickness, the dispersion of the solvent and the separation of the solute occur quickly and the extruded solution does not break asunder but assumes the form of a continuous filament. When the liquid substance is just left flowing into blood, the extruded filament assumes an amorphous texture and contains minute scattered particles in a large proportion as found in the photograph inserted as FIG. 1 in Neurosurgeons 9, 229–239, 1990. For the purpose of imparting continuity to the extruded thread of the liquid substance, the practice of discharging the liquid substance in the form of a filament thereby synergistically promoting the separation of the solute and the dispersion of the solvent proves one ideal approach.

When the liquid substance has an X-ray contrast medium admixed therewith, the filamentous embolic material produced by the extrusion of the liquid substance can be easily located by the X-ray.

The method for using the catheter of this invention will be described below. First in the catheter 1, the lumen 50 serving to supply a liquid substance is filled with ethylene-vinyl alcohol copolymer/dimethyl sulfoxide (concentration 5 g/100 ml) as the liquid substance and the distal end 20 of catheter is guided into a cerebral aneurysm with the aid of a guide wire. With the catheter 1 kept in the ensuant state thereof, the ethylene-vinyl alcohol copolymer/dimethyl sulfoxide is further injected through the liquid substance-introducing port 32, an inlet for the liquid substance formed in the proximal end 30 of catheter, and discharged into the aneurysm through the discharge orifice 52 in the distal end 20 of catheter. In the part of the liquid substance freshly discharged from the catheter, dimethyl sulfoxide as the solvent is dispersed in the blood and the ethylene-vinyl alcohol copolymer is consequently extruded in the form of a continuous filament. When the injection of the liquid substance is stopped, the liquid substance ceases to emanate from the catheter and the extrusion of the liquid substance terminates and the filament becomes broken. Since the discharge orifice is so small as to fall in the range of 10 to 100 $\mu m$, the extruded filament is very thin, soft, and supple and, therefore, is caused to gather into a round mass. This round mass of the filament induces formation of thrombus and eventually occludes the aneurysm.

In a concrete example, an embolectomy catheter of this invention was obtained by forming a tube (0.8 mm in inside diameter and 0.99 mm in outside diameter) of a thermoplastic polyester elastomer in a total length of 1,250 mm, joining a connector (hub) to the proximal end of the tube and, at the same time, thermally molding the distal end of the tube into a nozzle 0.2 mm in outside diameter, 0.1 mm in inside diameter, and 2.5 mm in length.

A liquid substance intended as the raw material for a filamentous embolic material was obtained by dissolving 5 g of an ethylene-vinyl alcohol copolymer (EVA having an ethylene content of 33 mol %, produced by Kuraray Co., Ltd. and marketed under product code of "EC-R101") in 100 ml of dimethyl sulfoxide (a reagent chemical produced by Wako Pure Chemical Industries, Ltd.). Preparatorily to the embolization, a solution solely of dimethyl sulfoxide was prepared as a protecting agent for the liquid substance. When the liquid substance is of such a type that an embolic material is produced in consequence of the separation of the solute from the solvent, the liquid substance-protecting agent is only required to be capable of precluding or restraining the dispersion of the solvent.

For the purpose of confirming the state of embolization with the extruded filament, the distal end of the catheter was dipped in a physiological saline solution, the interior of the catheter was primed with the physiological saline solution, and then 0.1 ml of the liquid substance-protecting agent (the solution solely of dimethyl sulfoxide) was injected through the proximal end of the catheter prior to the start of the extrusion of the liquid substance through the discharge orifice. Then, a syringe having an inner volume of 1 ml and filled with the liquid substance was connected to the proximal end connector and the syringe was manually compressed to effect discharge of the liquid substance through the nozzle tip of the catheter.

As a result, the nozzle tip began to emit a thread of the liquid substance. A continuous filament 0.1 mm to 0.2 mm in outside diameter and 150 mm in length began to zigzag immediately after the extrusion and at once gathered from the distal end side backward and formed a round network mass of filament. The end of the extruded filament could be removed from the nozzle by interrupting the exertion of pressure and giving a slight pull at the catheter. Since the liquid substance emanated in the form of a continuous filament from the discharge orifice, no part of this substance was found to separate and float as extraneous matter. The time intervened between the time the injection of the liquid substance was started and the time it was terminated was not more than 5 seconds.

As a control, the procedure described above was repeated, excepting a catheter (made of a thermoplastic polyester elastomer and measuring 0.8 mm in inside diameter, 0.99 mm in outside diameter, and 1,250 mm in length) not provided with the nozzle mentioned above was used to inject the same liquid substance as mentioned above. Then, the physiological saline solution was visually examined in search of a sign of the formation of a precipitate (embolic material) in the solution. The examination resulted in detection of a plurality of lumps of varying sizes. When the pressure applied to the liquid solution was continued in an effort to discharge the liquid substance in the form of a continuous filament, the amount of the precipitate increased and the formation of numerous granules was rather promoted. These results indicate the possibility that the embolic material flowed out of the aneurysm in an unduly large amount and the granules similarly flowed out and the extraneous substances so departing from the aneurysm would entail a complication of embolizing other normal blood vessels.

Figure 8A:
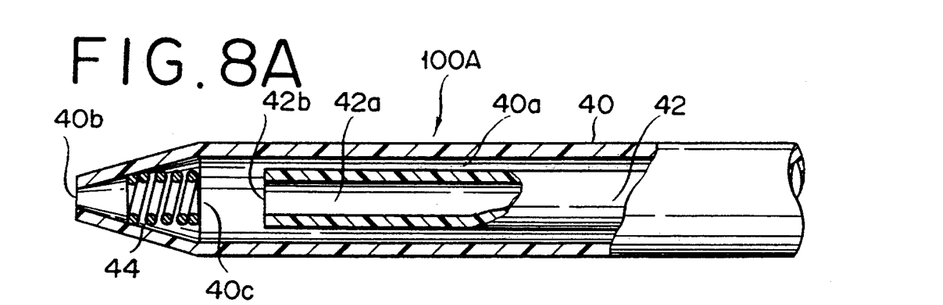
FIG. 8A is a cross section of the distal end of the embolectomy grade catheter of this invention.
Figure 8B:
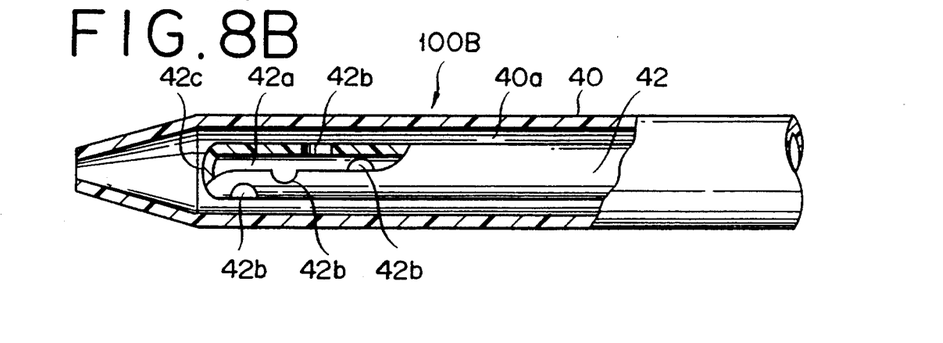
FIG. 8B is a cross section illustrating the distal end of the embolectomy grade catheter as another embodiment of this invention.

By way of illustration of another example of the embolectomy catheter of this invention, the distal end of an embolectomy catheter 100 which is composed of a main body part of catheter, a distal end of catheter, and a proximal end (operating part) of catheter similarly to the embolectomy grade catheter 1 of the embodiment of FIGS. 1 and 1B is depicted in the form of a partial cross section in FIGS. 8A and 8B.

An embolectomy grade catheter 100A illustrated in FIG. 8A is composed of an outer tube 40 and an inner tube 42. The inner tube 42 is contained inside the outer tube 40. The empty space defined by the outer surface of the inner tube 42 and the inner surface of the outer tube 40 constitutes a lumen 40a. The outer tube 40 opens at the distal end thereof and this opening 40b communicates with the lumen 40a. The distal end of the outer tube 40 has a tapered shape. In the inner tube 42, the lumen 42a opens at the distal end thereof and this opening 42b is separated from the opening 40b of the outer tube 40 by a prescribed distance toward the basal end side. The empty space enclosed with the inner wall of the outer tube 40 between the opening 42b of the inner tube 42 and the opening 40b of the outer tube 40 constitutes a lumen 40c. The distal end side of the lumen 40c narrows in the direction of the distal end.

A liquid substance is introduced into the lumen 40A and other liquid substance which reactively solidifies the liquid substance just mentioned as described specifically hereinafter is introduced into the lumen 42a. In the lumen 40c which serves to mix the two liquid substances, these liquid substances react and begin to solidify. A coil 44 provided in the lumen 40c fulfills the function of stirring the two liquid substances. By thus promoting the mixture of the liquid substances by the stirring, the mixture emitted through the opening 40b is enabled to form a continuous solid line infallibly.

An embolectomy catheter 100B illustrated in FIG. 8B comprises an outer tube 40 and an inner tube 42. The inner tube 42 is contained in the outer tube 40 and the empty space defined by the outer surface of the inner tube 42 and the inner surface of the outer tube 40 constitutes a lumen 40a. The outer tube 40 opens at the distal end thereof and this opening 40b communicates with the lumen 40a. The distal end of the outer tube 40 has a forwardly tapered shape. In the inner tube 42, the lumen 42a is occluded in a distal end 42c thereof. A plurality of openings 42b are provided in the wall of the inner tube 42. The openings 42b are not arranged on one axial line but are staggered. The distal end 42c of the inner tube 42 is separated by a prescribed distance toward the basal end side from the opening 40b of the outer tube 40. The empty space enclosed with the inner wall of the outer tube 40 between the distal end 42c of the inner tube 42 and the opening 40b of the outer tube 40 constitutes the lumen 40c. The distal end side of the lumen 40c narrows in the direction of the distal end thereof.

The liquid substance is introduced into the lumen 40a and the other liquid substance which reacts with the liquid substance just mentioned and solidifies it as specifically described hereinafter is introduced into the lumen 42a. In the lumen 40c which serves to mix the two liquid substances, these liquid substances react and begin to solidify. Since the openings 42b are staggered relative to the axial line, the reactive liquid can be mixed evenly with the liquid substance flowing through the lumen 40a. The length of the lumen 40c in the axial direction can be adjusted, depending on the time required for the reaction of the two liquid substances.

The liquid substances to be used in the present example are a combination of a reactive liquid substance and other liquid substance capable of reactively hardening the reactive liquid substance just mentioned. These two liquid substances are separately introduced through respective independent lumens to a common distal end thereof and are mixed in the distal end. The resultant mixture is discharged and solidified to form a filament. The combinations of a reactive liquid substance and other liquid substance capable of reactively hardening the reactive liquid substance which are effectively usable in the present embodiment include a combination between an epoxy type two-component curing resin as a principal component and a curing agent and a combination between an acryl type two-component curing resin as a principal component and a curing agent, for example.

The catheter is provided in the distal end thereof with a discharge nozzle which mixes the two liquid substances supplied thereto through the two independent lumens and emits the resultant mixture for the sake of extrusion into a filament. The length between the point of confluence of the two liquid substances and the opening in the distal end of the discharge nozzle can be suitably varied depending on the time required for the hardening of the liquid substances. Similarly to the other embodiments, the catheter of this embodiment may be provided with an opening for a lumen to be used for the insertion of a guide wire or an endoscope. In this case, two inlets for the injection of the two liquid substances and one inlet for the insertion of a guide wire or an endoscope are provided in the proximal end (operating part) of catheter.

The catheter illustrated in FIGS. 8A and 8B may be inserted through a prescribed lumen in the other catheter adapted to have the distal end thereof indwelt inside a aneurysm as illustrated in FIG. 6 and the distal end of the inserted catheter may be protruded forward from the other catheter.

Now, the method for using the catheter of the present embodiment will be described. First, in the catheter body, one of the lumens to be used for supplying liquid substances is filled with the reactive liquid substance as a principal agent and the other lumen filled with the other liquid substance as a curing agent. The discharge orifice is filled preparatorily with physiological saline solution for the purpose of precluding the two liquid substances from being mixed before extrusion through the discharge orifice. With the catheter held in the ensuant state, the distal end of catheter is guided into the cerebral aneurysm with the aid of a guide wire. The liquid substances are evenly injected through the inlets formed in the proximal end (operating part) of catheter for the introduction of such liquid substances. As a result, the two reactive substances are moved to the discharge orifice and then, after the release of the physical saline solution into blood, they are mixed in the discharge orifice, hardened, and continuously discharged in the form of a filament. When the injection of the liquid substances is stopped, the extrusion of the resultant mixture terminates and the extruded filament breaks because the supply of the reactive substances is stopped. It is desirable to comprehend the volume of the pertinent aneurysm in advance of the use of the catheter, compute the amounts of the two substances to be injected, and then start the injection of the two substances.

The discharge orifice is so small as to fall in the range of 50 to 200 μm. The extruded filament, therefore, is very thin, soft, and supple and is allowed to gather into a round mass inside the aneurysm, induce the occurrence of thrombus, and effect occlusion of the aneurysm.

Figure 9A:
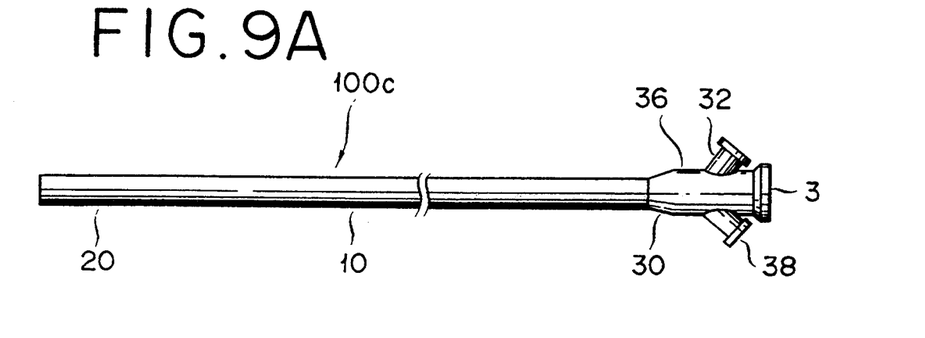
FIG. 9A is an overall perspective view of the embolectomy grade catheter of this invention.

As another embodiment of the invention, an embolectomy catheter illustrated in FIGS. 9A and 9B will be explained. In this diagram and the diagrams of FIGS. 1A and 1B and FIG. 3, like reference numerals refer to like parts. An embolectomy grade catheter illustrated in FIG. 9A comprises a main body 10 of catheter, a distal end 20 of catheter, and a proximal end (operating part) 30 of catheter. The proximal end 30 comprises a hub 36 which is composed of a liquid substance-introducing port 32, a guide wire port 34, and a light source connection port 38 intended to supply light to an optical fiber.

Since the boundary part between the main body part 10 and the distal end 20 is constructed as illustrated in FIGS. 2A and 2B, the main body 10 possesses high rigidity and excels in the ability to be forced into the blood vessel and the distal end 20 is soft and excels in the ability to be followed by the wall of the blood vessel.

Figure 9B:
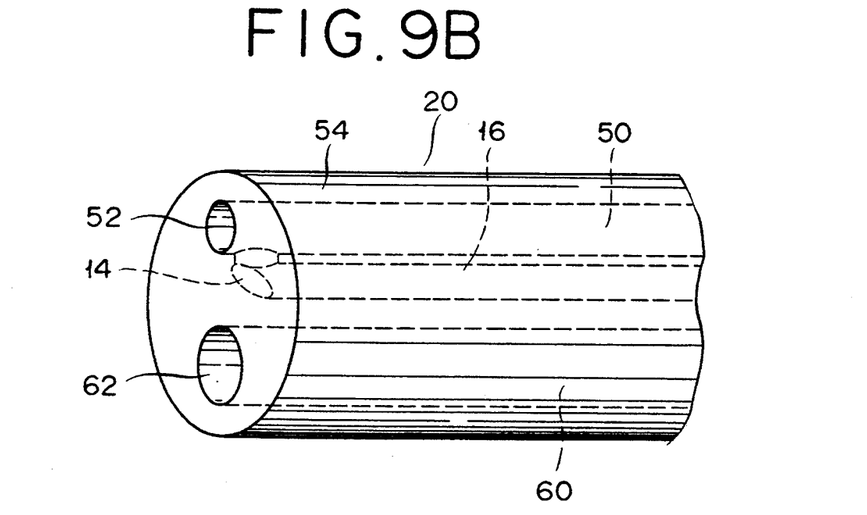
FIG. 9B is a magnified perspective view of the distal end of the catheter shown in FIG. 9A.

The distal end 20 of catheter of the present embodiment is provided, as illustrated in FIG. 9B, with a discharge nozzle 54 which comprises a discharge orifice 52 for discharging liquid substances and a distal end 16 of optical fiber. In this arrangement, the liquid substances are irradiated with light before they are discharged from the catheter. The distal end of the optical fiber is cut at an acute angle. The cut face 14 forms a mirror and reflects a light which has advanced through the optical fiber, changes the path of light, and illuminates the interior of the discharge orifice 52 of the lumen 50 adjoining the cut face 14 and serving to introduce the liquid substance.

The discharge nozzle 54 of the present catheter 100 is not tapered on the distal end side thereof. The present embodiment does not discriminate the discharge nozzle on account of its shape so long as the discharge nozzle enables the mixture of liquid substances to be hardened by exposure to light and the extruded filament to retain continuity. When the formation of the filament benefits from a taper to be formed in the distal end of the discharge nozzle, it is wise to impart the taper to the distal end.

Similarly to the catheters of the other embodiments, the catheter of the present embodiment has an opening 62 provided for the lumen 60 which permits insertion of a guide wire or an endoscope.

The optical fiber functions better with a larger thickness because the thickness of the optical fiber bears on the amount of light impinging on the distal end. If the optical fiber has an unduly large thickness, however, it deprives the catheter itself of softness. When the catheter has a diameter in the range of 0.5 to 1 mm, for example, the optical fiber is desired to have a thickness in the approximate range of 50 to 400 μm. At times, a neat bundle of a plurality of extremely thin optical fibers serves well. The total of the cross sections of the individual optical fibers in the bundle is desired to equal the cross section of the single optical fiber described above.

The liquid substance to be used in the present embodiment is a photoreaction type liquid substance which hardens on exposure to light. As concrete examples of the photoreaction type liquid substance effectively usable herein, photosensitive resins of the light radical addition type and the light cationic polymerization type besides such acryl type light-curing resins as polyester acrylates, urethane acrylates, acrylic esters, and methacrylic esters may be cited.

The proximal end (operating part) 30 of catheter is provided with a light source (not shown) which is connected to the rear end of the optical fiber and adapted to supply light. It is further provided with a liquid substance-introducing port 32 and a guide wire port 34.

The wavelength of the light source is varied to suit the particular quality of the liquid substance. Specifically, a light source having a wavelength in the range of 300 to 500 nm is used advantageously where the liquid substance is a polyester acrylate or urethane acrylate. The resins which are set on exposure to light include light radical addition type and light cationic polymerization type photosensitive resins besides such acryl type light-curing resins as acrylic esters and methacrylic esters, for example.

The method for using the catheter of the present embodiment will be described. First, the lumen 50 of the catheter 100C for supplying a light substance is filled preparatorily with a photoreaction type liquid substance. With the catheter kept in the ensuant state, the distal end 20 of catheter is guided into the cerebral aneurysm with the aid of a guide wire. When the liquid substance is evenly injected through the liquid substance-introducing port 32 in the proximal end (operating part) 30 of catheter, the discharge orifice 52 begins to emit this liquid substance. When the light source is turned on at the same time that the emission of the liquid substance is started, the emitted thread of the liquid substance begins to harden and the hardened thread grows into a continuous filament. This filament is cut of by first turning off the light source and then stopping the injection of the liquid substance.

Figure 10:
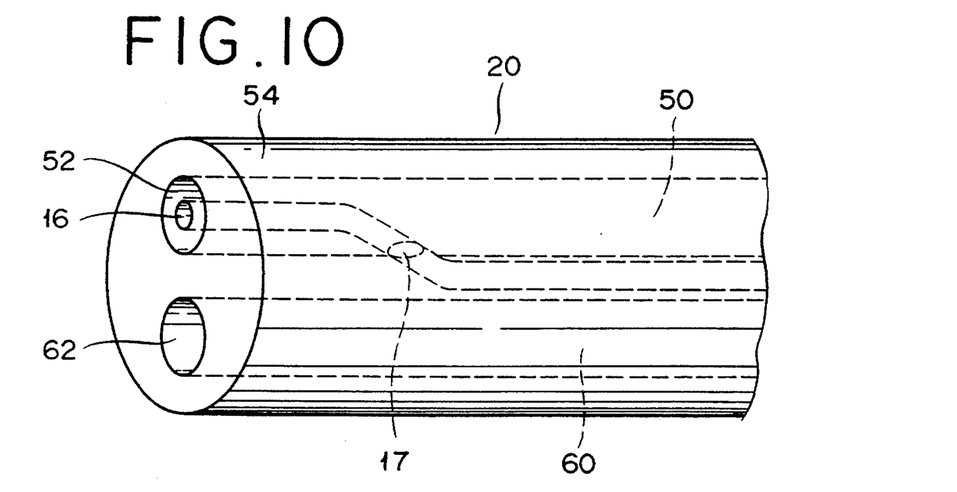
FIG. 10 is a perspective view of the distal end of the embolectomy grade catheter of this invention.

The distal end of the catheter of the embodiment of FIG. 9A and 9B will be described with respect to the embodiment constructed as illustrated in FIG. 10. In the embodiment of FIG. 20, the distal end 20 of catheter is provided with a discharge nozzle 54 which comprises a discharge orifice 52 for extruding the liquid substance and a distal end 16 of optical fiber adapted to irradiate the discharge orifice 52 with light. The irradiation with the light is effected immediately before the liquid substance introduced through the lumen 50 is discharged.

The distal end of the optical fiber is located at the coaxial center of the discharge orifice. The photoreaction type substance is discharged in such a manner that the emanating stream thereof engulfs the distal end of the optical fiber and consequently exposes itself to the light thrown out of the optical fiber. The construction is at an advantage in enabling the light source to be concurrently utilized as a light source for the endoscope.

The optical fiber comprises a core and a peripheral clad having a smaller refractive index than the core. It is so designed as to contain the light within the fiber. In the distal end 20 of catheter, the portion of the optical fiber past a point 17 at which the optical fiber thrusts in the lumen 50 for the introduction of the liquid substance is not provided with the clad. In the discharge nozzle 54, therefore, the light is projected radially from the portion of the optical fiber which is devoid of the clad. As a result, even a liquid substance which interjects no infinitesimal interval between the time the reaction begins and the time the hardening terminates is allowed to be used in the catheter of this embodiment by adjusting the length of the unclad portion of the optical fiber. Thus, the catheter of this embodiment allows ample liberty of choice of liquid substances.

The catheter is further provided, similarly to the catheters of the other embodiments described above, with an opening 62 for the lumen 60 which permits insertion of a guide wire or an endoscope.

Here, two working examples have been disclosed. The present embodiment does not particularly discriminate the catheter on account of its shape so long as the photoreaction type liquid substance is exposed to the light passed through the optical fiber immediately before it is extruded from the discharge orifice.

Figure 11:
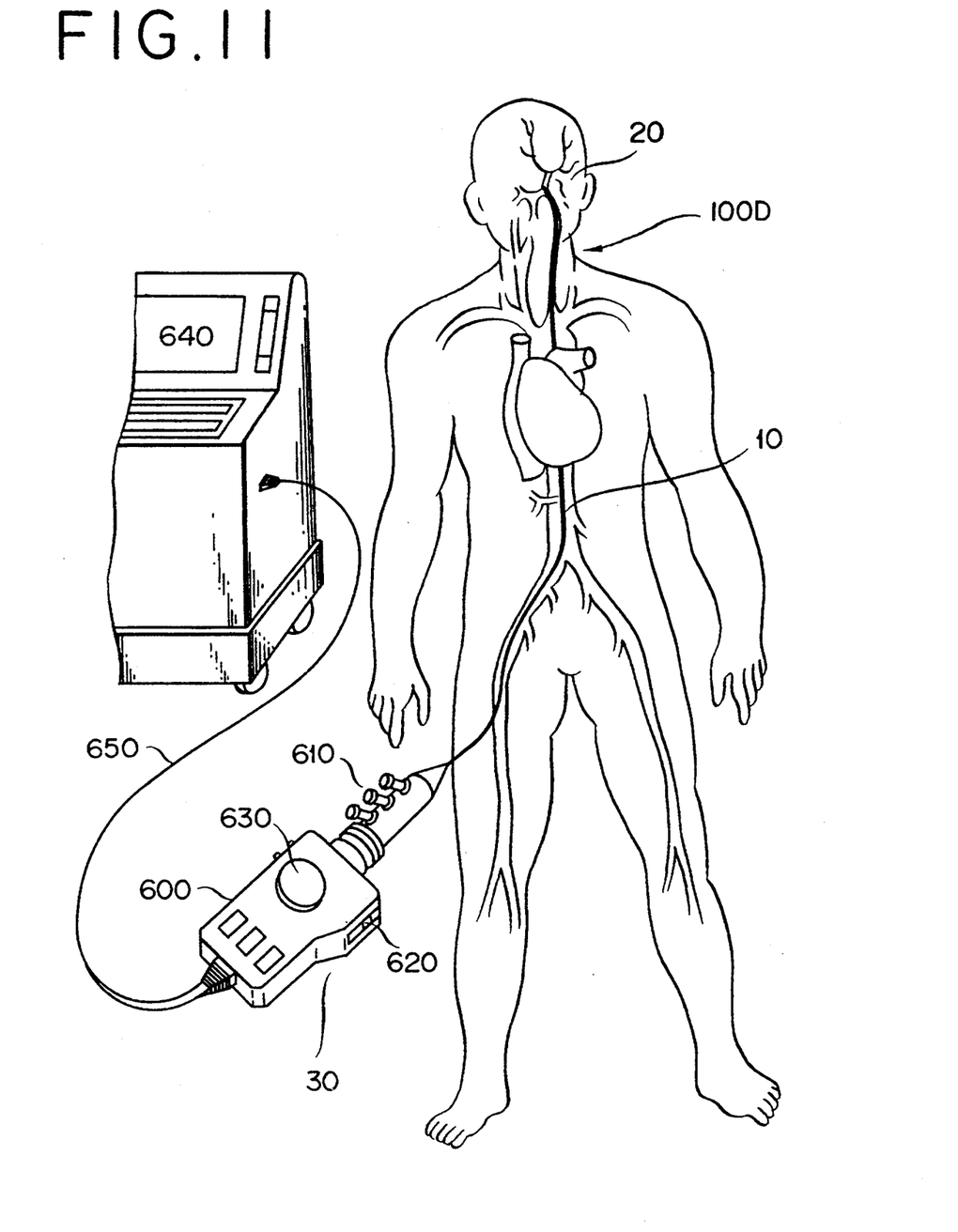
FIG. 11 is a model diagram illustrating the embolectomy grade catheter of this invention as inserted into a human body.
Figure 12:
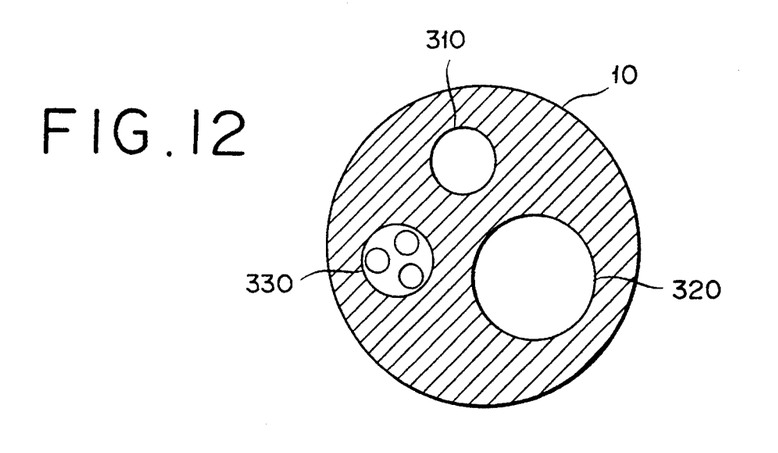
FIG. 12 is a cross section of the main body part of the embolectomy grade catheter of this invention.

Other working examples of this invention will be described below with reference to FIG. 11, FIG. 12, and FIG. 13. FIG. 11 is a model diagram illustrating a catheter 100D of the present embodiment as indwelt in a cerebral artery. The catheter 100D is composed of a main body 10 of catheter, a distal end 20 of catheter, and a proximal end 30 of catheter. Now, the main body 10 of catheter will be described below with reference to FIG. 12 depicting the main body in a cross section. The main body 10 of catheter is provided with an inner hole 310 for supplying a liquid substance for extrusion to a micropump 400 (FIG. 13) which will be specifically described hereinafter, an insertion hole 320 permitting insertion of a guide wire or an endoscope, and a plurality of optical fibers 330 for supplying light to a photoelectric device 450 which will be specifically described hereinafter.

Figure 13:
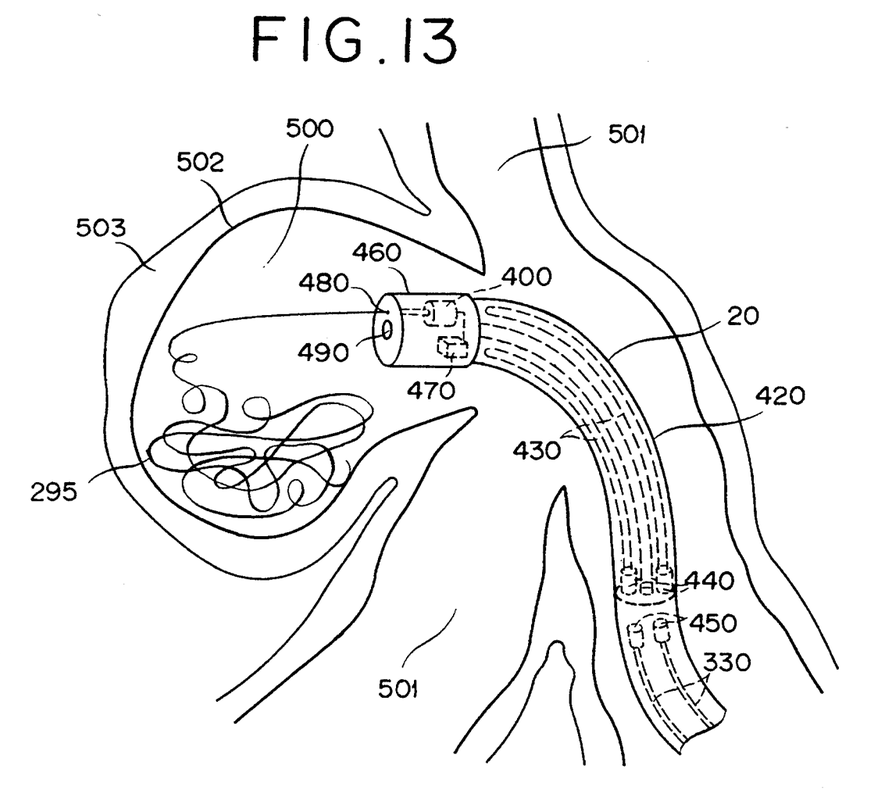
FIG. 13 is a perspective view of the distal end of the catheter of this invention.

FIG. 13 illustrates the condition of use of the distal end 20 of catheter. The distal end 20 of catheter is joined to the main body part of catheter through the medium of a joint part 420 which is formed of a shape memory alloy. In this shape memory joint, two shape memory alloy wires 430, 430 are opposed to each other relative to the inner cavity of the catheter, microheater arrays 440, 440 are attached one each to the shape memory alloy wires 430, 430, and the microheater arrays 440 and 440 are connected one each to photoelectric devices 450 and 450. The photoelectric devices, on exposure to the light supplied by an optical fiber 330, generates electricity. This electric power heats the microheater arrays 440, 440 and causes the shape memory alloy wires to change shape in a prescribed pattern. This mechanism is utilized in delicately altering the direction of the distal end 20 of catheter. In this arrangement, the shape memory alloy wires 430 are laid out in the form of a loop inside the inner cavity of the catheter and heated by being energized through the medium of the microheater arrays.

Further, a distal end 460 in the distal end 20 of catheter is provided with the micropump 400, a photoelectric device 470 serving as a power source for driving the micropump 400, a micronozzle 480 for extrusion connected to the micropump 400, and an opening 490 of insertion hole.

The optical fiber (not shown) communicating with the proximal end of catheter via the main body 10 of catheter is connected to the photoelectric device 470. The light forwarded from the proximal end of catheter through the optical fiber is transformed by the photoelectric device 470 into a voltage. This voltage drives the micropump 400.

The micropump 400 is a diaphragm type micropump. The micropump 400 imposes pressure in the distal end on the liquid substance in the process of transfer to the micronozzle 480 for extrusion for the purpose of imparting shearing stress to the liquid substance being discharged.

The liquid substance which is used in the present embodiment may be fibroin which becomes extrusible on exposure to shearing stress or any of the substances of the solute separation type cited previously.

The opening 490 of insertion hole is an opening of the hole which communicates with the proximal end of catheter and permits insertion of a guide wire or an endoscope. The distal end of the guide wire is thrust out of this opening and used for selecting blood vessels or the endoscope is similarly protruded from the opening and operated for observation of blood vessels and sites of disease.

In the proximal end 30 of catheter, a grip part 600 so shaped as to allow easy handling, an injection part 610 for admitting a liquid substance destined to be extruded, a switch 620 for the operation of discharge, an operating ball 630 for controlling the direction of energization and flexure of a multijoint made of shape memory alloy, etc. The proximal end of catheter is further connected with a cable 650 to a monitor part 640 which comprises a light source unit serving the endoscope and the discharge device and an image display device enabling an operator to view the image obtained with the endoscope.

The operation of the embolectomy grade catheter 100D which is constructed as illustrated above will be described below with respect to a typical procedure to be actually adopted.

(1) The distal end 20 of catheter is delivered to the interior 500 of a cerebral aneurysm as guided with a guide wire and indwelt therein. In cases where the guide wire encounters difficulty in selecting branches in the blood vessel or in making a delicate location in the interior 500 of the aneurysm, the direction of the distal end 20 can be delicately altered by transforming the light from the optical fiber 330 into an electric current through the medium of the photoelectric device, heating the microheater arrays 440 with the electric current, and changing the shape of the shape memory alloy wires as required.

(2) The liquid to be extruded is supplied through the inner cavity 310 adapted to supply this liquid to the micropump 400 after the distal end has reached the interior 500 of cerebral aneurysm.

(3) The photoelectric device 470 is operated to actuate the micropump 400 and exalt the inner pressure of the chamber. Then, the liquid for extrusion (the solution of fibroin) is discharged under high pressure to give rise to an embolic material 295.

(4) The filamentous embolic material 295 which has been extrusion molded has continuity and, therefore, keeps clear of the possibility of breaking asunder and leaking to an exterior 501 of the aneurysm. The possibility of the extruded filament imposing powerful pressure on a wall 503 of aneurysm and causing a fracture therein is nil.

(5) When the material for extrusion abounds in affinity for or reactivity with an inner membrane 502 of aneurysm, the extruded filament adheres fast to a wall 503 of aneurysm and, at the same time, a round mass 295 of the filamentous embolic material reacts with blood and transforms into a solidified mass and effects perfect occlusion of the interior 500 of aneurysm.

(6) The formation of the embolic material 295 is terminated by suspending the discharge of the liquid for extrusion. This termination of the formation is confirmed with the aid of the endoscope which is inserted through the hole 320 into the interior 500 of aneurysm.

The endoscope serves well in the location of the distal end of catheter before the extrusion and the confirmation of the process of extrusion. It is self-evident that the procedure described above can be substituted by other proper procedure.

The filamentous embolic material which is produced by the embolectomy catheter of this invention as described above is desired to have a diameter in the range of 0.01 to 1.0 mm, preferably 0.1 to 0.5 mm. A variation in the outside diameter of this filamentous embolic material has no adverse effect on the operation of embolectomy so long as this variation has continuity fit for the convenience of handling. When the filamentous embolic material is discharged in a crimped form from the catheter, it is at an advantage in readily gathering into a round mass and filling the interior of aneurysm from the center outward. The filament of the embolic material is desired to have a thickness in the range of 1 to 100 deniers (1 denier=thickness of a filament measuring 450 m in length and having a mass of 50 mg), preferably 10 to 50 deniers.

What is claimed is:

1. An embolectomy catheter containing a lumen for the introduction of a liquid substance, and a filament forming device provided in a distal end of the catheter and arranged to receive the liquid substance introduced through said lumen for extruding said received liquid substance in the form of a filamentous embolic material, and wherein said filament forming device is dimensioned and arranged to extrude said liquid substance such that said liquid substance hardens in the form of said filamentous material immediately after exiting from said filament forming device at the distal end of the catheter.

2. A catheter according to claim 1, wherein said lumen for the introduction of said liquid substance opens in both a distal end and a proximal end part of said catheter.

3. A catheter according to claim 2, further comprising at least one further lumen which is separated from said lumen for the introduction of said liquid substance.

4. A catheter according to claim 3, wherein said filament forming device includes discharge means.

5. A catheter according to claim 2, wherein:
said liquid substance comprises a reactive liquid substance and another liquid substance capable of reactively hardening said reactive liquid substance;
said catheter includes a further lumen;
said reactive and another liquid substances are introduced to said distal end through respective lumens; and
said filament forming device forms said filamentous embolic material by mixing said reactive liquid substance with said another liquid substance capable of reactively hardening said reactive liquid substance.

6. A catheter according to claim 2, wherein:
said liquid substance is a photoreaction type liquid substance capable of being hardened by exposure to light; and
said filament forming device comprises light emission means for reactively hardening said photoreaction type liquid substance.

7. A catheter according to claim 1, wherein said filament forming device includes a mechanism for applying a shearing stress to said liquid substance to form said filamentous embolic material.

8. A catheter according to claim 1, wherein said filament forming device includes an extruding device dimensioned to extrude said liquid substance such that said extruded filamentous embolic material has a filament thickness in the range of 1 to 100 deniers.

9. A catheter according to claim 1, wherein said filament forming device comprises:
a reservoir part formed inside said catheter for storing the liquid substance;
means for imposing pressure on said reservoir part;
a lumen arranged for intercommunication between the exterior of said catheter and said reservoir part; and
means for transforming a mobile liquid substance stored in said reservoir part into a continuous filament.

10. A catheter according to claim 1, wherein the catheter comprises a main body portion which is relatively rigid, a distal end portion which is relatively soft, and said distal end portion including said filament forming device for forming said filamentous embolic material.

11. A catheter according to claim 1, wherein said catheter has a coating layer on an outer surface thereof, said coating layer having biocompatibility and lubricity.

12. A catheter according to claim 4, wherein said discharge means comprises a radially contracted distal end portion of said lumen for the introduction of said liquid substance.

13. A catheter according to claim 1, wherein said liquid substance comprises a resinous solute which is insoluble in blood and a solvent.

14. A catheter according to claim 4, wherein said discharge means comprises a nozzle for discharging a filamentous embolic material having a diameter of 0.01 to 1.0 mm.

15. A catheter according to claim 4, wherein said discharge means comprises a nozzle for discharging a filamentous embolic material having a diameter of 0.1 to 1.5 mm.

16. A catheter according to claim 4, wherein said discharge means comprises a nozzle having a discharge orifice of about 10 to 100 μm.

17. A catheter according to claim 1, wherein said filament forming device includes an extruding device dimensioned to extrude said liquid substance such that said extruded filamentous embolic material has a filament thickness in the range of 10 to 50 deniers.

18. An embolectomy catheter containing a lumen for the introduction of a liquid substance, and a filament forming device provided in a distal end of the catheter and arranged to receive the liquid substance introduced through said lumen for extruding said received liquid substance in the form of a filamentous embolic material, and wherein:

said liquid substance is a photoreaction type liquid substance capable of being hardened by exposure to light; and said filament forming device comprises light emission means for reactively hardening said photoreaction type liquid substance.

19. A catheter according to claim 18, wherein said lumen for the introduction of said liquid substance opens in both a distal end and a proximal end part of said catheter.

20. A catheter according to claim 18, further comprising at least one further lumen which is separated from said lumen for the introduction of said liquid substance.

21. A catheter according to claim 18, wherein the catheter comprises a main body portion which is relatively rigid, a distal end portion which is relatively soft, and said distal end portion including said filament forming device for forming said filamentous embolic material.

22. An embolectomy catheter containing a lumen for the introduction of a liquid substance, and a filament forming device provided in a distal end of the catheter and arranged to receive the liquid substance introduced through said lumen for extruding said received liquid substance in the form of a filamentous embolic material, and wherein said filament forming device comprises:

a reservoir part formed inside said catheter for storing the liquid substance;

means for imposing pressure on said reservoir part;

a lumen arranged for intercommunication between the exterior of said catheter and said reservoir part; and means for transforming a mobile liquid substance stored in said reservoir part into a continuous filament.

* * * * *

UNITED STATES PATENT AND TRADEMARK OFFICE
CERTIFICATE OF CORRECTION

PATENT NO.  : 5,443,454
DATED       : August 22, 1995
INVENTOR(S) : TANABE et al.

It is certified that error appears in the above-indentified patent and that said Letters Patent is hereby corrected as shown below:

```
Title page, Item [56] References Cited, under
          "OTHER PUBLICATIONS", (in colomn 2, line 6)
          after "Medical Tribune" change:

"pp.46≧47" to --pp.46-47--

Column 6, line 53, after "which" insert --comprises--.

Column 13, line 25, "FIGS. 1" should be --FIGS. 1A--
```

Signed and Sealed this

Twenty-ninth Day of October 1996

Attest:

BRUCE LEHMAN

*Attesting Officer*        *Commissioner of Patents and Trademarks*